United States Patent [19]
Leveson et al.

[11] Patent Number: 5,350,565
[45] Date of Patent: Sep. 27, 1994

[54] SYSTEM FOR THE DETECTION OF NOXIOUS CONTAMINANTS IN BEVERAGE AND POTABLE WATER CONTAINERS

[75] Inventors: Richard C. Leveson, Willowdale; John D. Laslavic, Etobicoke; Nicholas J. Barker, Mariposa Township, all of Canada

[73] Assignee: Photovac Centre, Inc., Ontario, Canada

[21] Appl. No.: 987,897

[22] Filed: Dec. 3, 1992

[51] Int. Cl.[5] .................... G01N 21/01; G01N 21/47; B07C 5/10
[52] U.S. Cl. ...................... 422/64; 209/3.1; 209/524; 422/63; 436/111; 436/113
[58] Field of Search ............ 422/64, 82.01, 82.05, 422/82.09, 91, 98, 99; 436/111, 113, 153; 209/3.1, 523, 524; 222/144

[56] References Cited

U.S. PATENT DOCUMENTS

| | | | |
|---|---|---|---|
| 3,970,430 | 7/1976 | Reader et al. | 422/83 X |
| 4,083,637 | 4/1978 | Ellinger et al. | 356/240 |
| 4,413,185 | 11/1983 | Leveson et al. | 250/423 |
| 4,830,192 | 5/1989 | Plester et al. | 209/3.1 |
| 4,855,110 | 8/1989 | Marker et al. | 422/102 |
| 4,858,768 | 8/1989 | Plester et al. | 209/3.01 |
| 4,880,120 | 11/1989 | Myers et al. | 209/3.01 |
| 5,067,616 | 11/1991 | Plester et al. | 209/3.01 |
| 5,202,932 | 4/1993 | Cambier et al. | 382/8 |

Primary Examiner—Robert J. Warden
Assistant Examiner—Robert Carpenter
Attorney, Agent, or Firm—Skjerven, Morrill, MacPherson, Franklin & Friel

[57] ABSTRACT

A device for detecting contaminants in returned bottles, particularly in a high-speed bottle line, is disclosed. In the preferred embodiment, a sample chamber is rotated on a carousel unit between top and bottom bulkheads. The surfaces of the bulkheads facing the chamber are flat and substantially parallel, and the chamber has two open ends which face the two bulkheads, respectively. A blast of air is directed into the mouth of the bottle to be sampled, forcing the contents of the bottle through an aperture in the lower bulkhead and into the sample chamber. In the preferred embodiment, the analyzer contains a UV absorption analyzer and a photoionization detector. The carousel unit contains four sample chambers which rotate between a sampling station, the two detectors, and a purge station. The analyzer is controlled by a computer which issues a reject instruction to a bottle reject mechanism if the level of contaminants detected by either detector exceeds a predetermined threshold. In an alternative embodiment, the level of chemically-bound ammonium radicals is detected by analyzing the same sample twice with one or two photoionization detectors. An alkaline substance is added to the sample between the measurements. Since the combination of an alkaline substance and ammonium radicals will free ammonia gas, a substantially higher reading during the second analysis indicates the presence of ammonium radicals.

19 Claims, 13 Drawing Sheets

SYSTEM FOR THE DETECTION OF NOXIOUS CONTAMINANTS IN BEVERAGE AND POTABLE WATER CONTAINERS

FIELD OF THE INVENTION

This invention relates to systems for detecting whether a returned bottle or other container has been used to hold noxious contaminants. It is particularly applicable to the analysis of plastic containers.

BACKGROUND OF THE INVENTION

There is a strong trend today, inspired by legal requirements in some areas, to employ reusable containers for soft drinks and mineral waters. This requirement is driven by both environmental and economic considerations. Soft drink bottles and other containers that have traditionally been made of glass are now increasingly being made from plastics.

Such containers may be used for a wide variety of purposes prior to their return. For example, returned containers are sometimes found to contain residues of gasoline, paint thinner or other noxious contaminants. Plastic containers are particularly prone to retaining such residues, even after washing. It is therefore very important that such contaminated containers be identified and discarded.

U.S. Pat. No. 4,830,192 to Plester et al. describes a method by which containers may be inspected for undesirable residues. The containers are partially filled with distilled water, agitated to ensure thorough mixing of any residues, and then inverted so as to pour the mixture into a cuvette for analysis. The method involves analysis carried out only in the liquid phase by a variety of physical methods, including ultraviolet (UV) visible absorption, a standard and well-known laboratory technique which has been in use for many years. The wavelengths are in the range 350–700 nm. Use of shorter UV wavelengths, of particular value in vapor phase analysis, is not described. This technique has the disadvantage of being time-consuming and requiring that each container be physically handled. Water must be added to and removed from each container, and then analyzed off-line.

For several years Photovac Incorporated of Ontario, Canada (the assignee of this application) and HNU Systems, Incorporated of Massachusetts have offered specialized products which are capable of analyzing a vapor sample, pumped from within a returned beverage container, to determine the level of organic vapor present. The analysis is performed by photoionization. The speed with which these units are able to analyze the samples is limited, however, primarily because the method of sampling requires pumping an air sample through an enclosed cell, taking a measurement, and then purging the contents. Given this limitation, multiple detectors and carousel-type container handling systems must be used in order to analyze containers moving rapidly through a production line.

SUMMARY OF THE INVENTION

In accordance with this invention, the vapor inside a container is removed for analysis by directing a jet of a gas (e.g., air) into the container. The gaseous jet forces the vapor inside the container into a sample chamber, which is open-ended so as to permit easy entry by the vapor expelled from the container. In a preferred embodiment, the sample chamber is formed by an open-ended cylinder which rotates on a carousel arrangement between two plates. A hole is provided in the lower plate to permit the vapor from the container to enter the cylinder, and a corresponding hole directly above the cylinder allows the vapor to flow easily into the cylinder.

As soon as the sample has entered the cylinder, the carousel rotates between the two plates, closing off the ends of the cylinder and trapping the sample.

The sample-containing cylinder may then be rotated to a number of stations for analysis by various techniques. For example, in a preferred embodiment, the sample is first rotated to a station in which a mirror is positioned at one end of the chamber and a transparent window is positioned at the other end of the chamber. A beam of ultraviolet (UV) light is directed into the cylinder and reflects off the mirror at one end of the cylinder. The UV light which emerges from the cylinder is then broken into constituent wavelengths which are analyzed and compared against the radiation produced by the UV source to determine whether the sampled vapor contains contaminants.

The sample chamber may then be rotated to a third station, where the sample is subjected to analysis by photoionization. One of the plates contains a hole which is aligned with an open end of the analysis chamber when it is located at the third station. The contents of the analysis chamber therefore migrate through the hole into a photoionization detector, where the sample is subjected to UV radiation as it passes between electrically-charged electrodes. Contaminants in the sample are ionized by the UV radiation, and the positive ions are repelled by the positively charged electrode, thereby producing a current which is detected. The photoionization chamber is open-ended so as to allow the sample to migrate quickly into the chamber for analysis.

The sample chamber may be rotated to other stations for additional types of analysis. In the final station, holes in both plates coincide with the ends of the cylinder, and the cylinder is purged by a fan or by a blast of a clean gas such as air. The sample chamber then rotates to the first station, and the cycle is repeated.

Some substances, such as ammonium compounds dissolved in a aqueous residue, are chemically-bound and not easily detected in analyzers which employ UV radiation. In an alternative embodiment, two analyzers are positioned at different points along the container line, and an alkaline solution is added to the containers between the two analyzers. This causes ammonia gas to be generated if ammonium compounds are present. The first analyzer provides data representative of the "background" level of contamination in the container, and these data are stored in a memory. The data are then compared with the data provided by the second analyzer, and if the second analyzer detects a substantially higher level of contamination (electric current), the computer concludes that the difference is attributable to bound ammonium radicals and issues an instruction to reject the container.

DESCRIPTION OF THE INVENTION

The system of this invention includes an analyzer, which is typically positioned along a container line, and a control network used to control the functions of the analyzer. Initially, the analyzer will be described.

Figure 1:
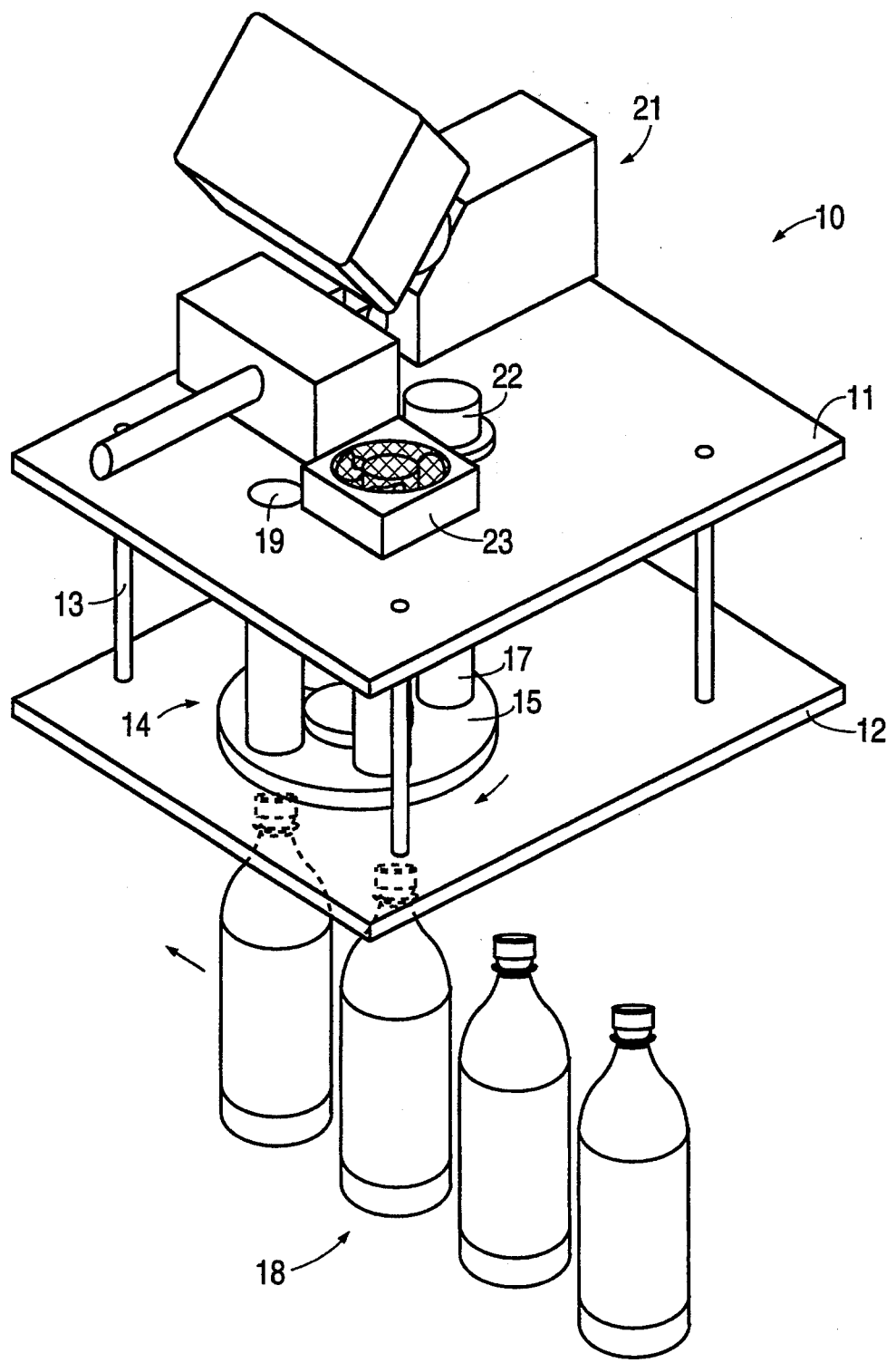
FIG. 1 illustrates a general view of a container analyzer in accordance with the invention.

FIG. 1 illustrates a general perspective view of a container analyzer 10, which in this embodiment is a bottle analyzer. The basic structure of analyzer 10 includes an upper bulkhead 11, a lower bulkhead 12 and four columns 13 which tie bulkheads 11 and 12 together rigidly and parallel to each other in fixed relationship. Between bulkheads 11 and 12 is positioned a carousel unit 14 which includes a bottom disk 15, and a top disk 16 (shown in FIG. 2), containing apertures into which are fitted four cylinders 17, which serve as sample chambers. Cylinders 17 are open-ended and coincide with apertures formed in bottom disk 15 and top disk 16. While cylinders 17 are shown as having circular cross sections, vessels having square or other cross sections may also be used. A stepper motor (not shown) rotates carousel 14, which is rotatably positioned between bulkheads 11 and 12 on a drive shaft 25 (FIG. 2) which forms a rotatable connection between bulkheads 11 and 12 and carousel unit 14. From the perspective of FIG. 1, carousel unit 14 rotates in a clockwise direction. A line of bottles 18 to be analyzed are transported in an upright position beneath lower bulkhead 12 by a conveyor system (not shown).

Figure 2:
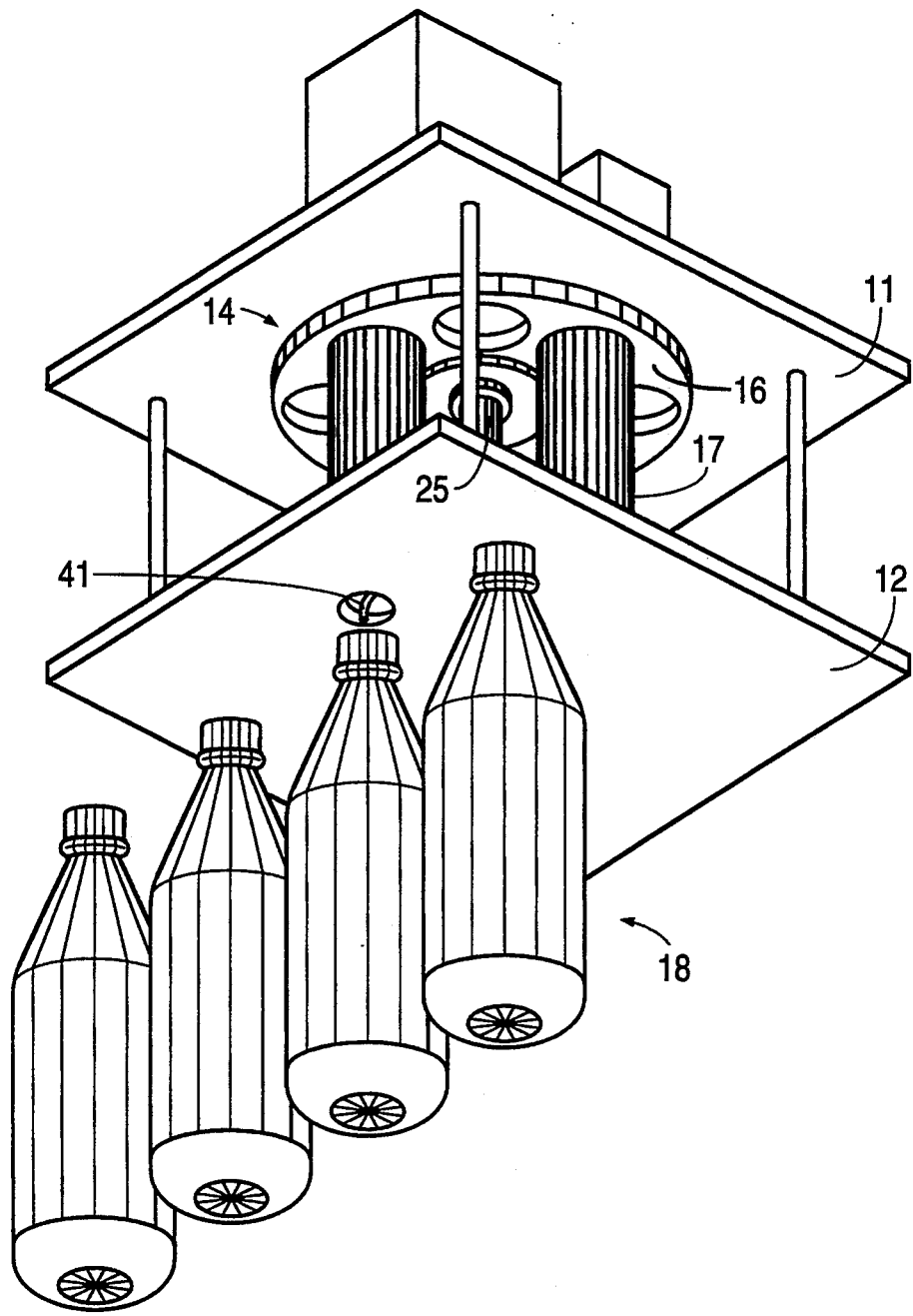
FIG. 2 illustrates a perspective view from underneath the container analyzer.

Carousel unit 14 rotates through four stations as the contents of bottles 18 are analyzed. The stations are defined by the components and structural features on the top of bulkhead 11. Referring again to FIG. 1, at Station 1 an aperture 19 is formed in bulkhead 11. As shown in FIG. 2, a similar aperture 20 is formed in bulkhead 12. At Station 2, a UV absorption (UVA) analyzer 21 is mounted on top of bulkhead 11. At Station 3, a fast photoionization detector (FPID) 22 is mounted on bulkhead 11. Finally, at Station 4, apertures similar to apertures 19 and 20 are formed in bulkheads 11 and 12, respectively, and a fan unit 23 is mounted on bulkhead 11.

Figure 3:
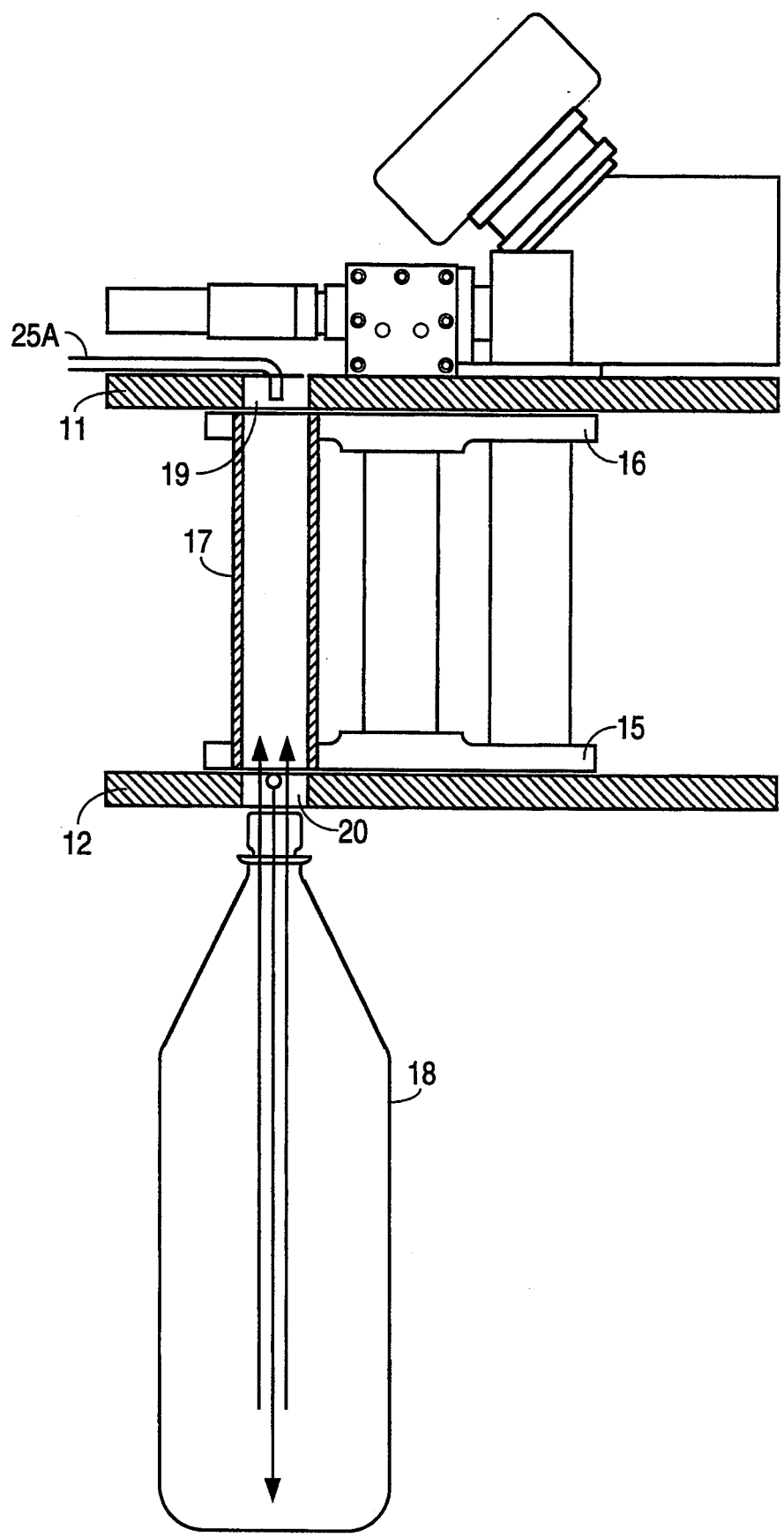
FIG. 3 illustrates a cross-sectional view of the fill station of the analyzer.

The following is a detailed description of the structures of and functions performed at each of Stations 1-4:

FIG. 3 illustrates a cross-sectional view of Station 1. As noted above, apertures 19 and 20 coincide with the open ends of one of cylinders 17. The inside diameters of apertures 19 and 20 are approximately equal to the inside diameter of cylinder 17. The mouth of one of bottles 18 is positioned just below the bottom surface of bulkhead 12. A tube 25A is connected to a supply of pressurized air or calibration gas through solenoid valves (not shown), and as described below, serves to fill cylinder 17 with one or the other of these gases for calibration when no bottles are present.

Figure 4:
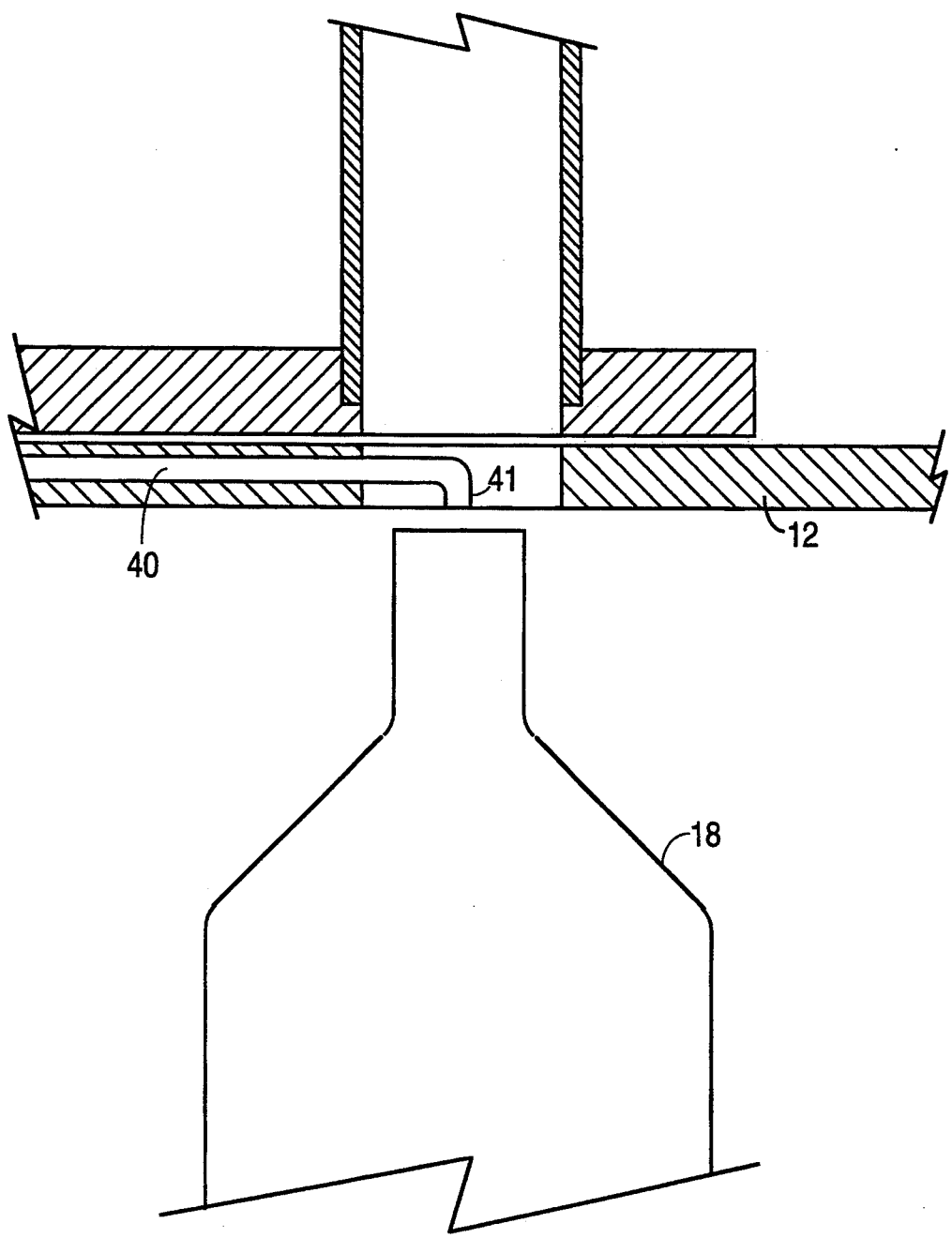
FIG. 4 illustrates a detailed cross-sectional view of the fill station.

As shown in FIG. 4, a tube 40 which terminates at a nozzle 41 is positioned in a groove in bulkhead 12, with nozzle 41 centered over the mouth of bottle 18 and directed vertically downward toward the inside of bottle 18. Tube 40 is connected to a supply of pressurized air, through a solenoid valve (not shown). As indicated by the arrows in FIG. 3, when the solenoid valve is actuated so as to release a blast of air through nozzle 41, the air forces the vapor within bottle 18 upward through aperture 20 and into cylinder 17. Aperture 19 ensures that the vapors are expelled readily into cylinder 17. The duration of the blast of air depends on the size of bottle 18, the time for which the bottle opening is beneath nozzle 41, and the air pressure used. In practice, it has been found that a 50 msec blast of air at a pressure of 40 psi is adequate to evacuate a standard 1.5 liter bottle.

As soon as the vapors inside bottle 18 have been forced into cylinder 17, the stepper motor which drives carousel unit 14 is actuated so as to move cylinder 17 to Station 2. As is apparent from FIG. 3, the clearance between upper bulkhead 11 and top disk 16, and between lower bulkhead 12 and bottom disk 15, respectively, is very small (preferably about 0.25 mm). Thus as soon as carousel 14 begins to rotate, the vapors are trapped inside cylinder 17 and very little leakage occurs out of the top and bottom of cylinder 17.

In a typical bottle line, bottles 18 move at a rate of 300 bottles/min, or 5 bottles/sec. Thus carousel unit 14 remains at each of Stations 1-4 only for about 120 msec, allowing about 80 msec for movement between stations.

Figure 5:
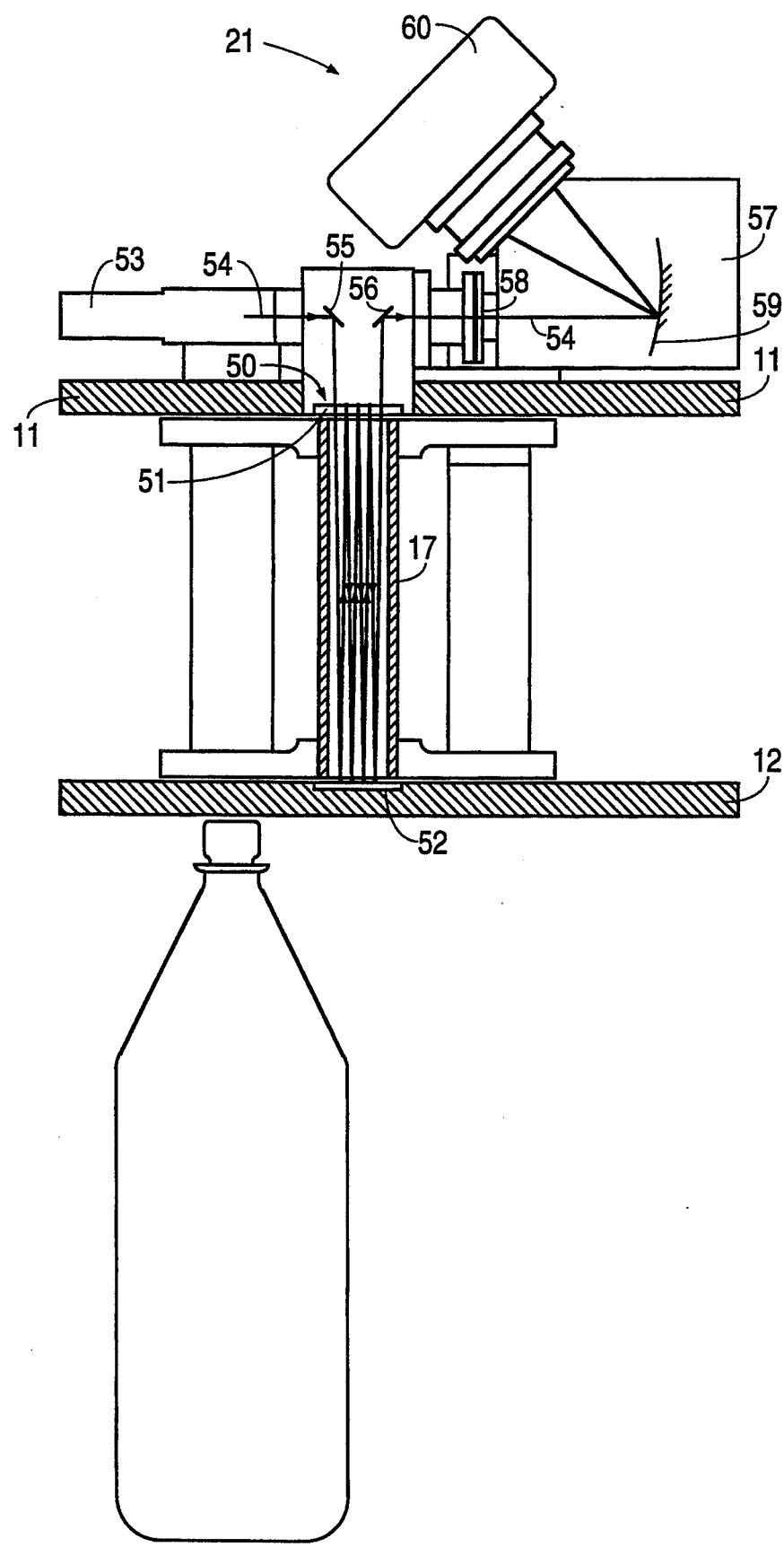
FIG. 5 illustrates a cross-sectional view of the UV absorption analyzer.

A cross-sectional view of Station 2, including UVA analyzer 21, is illustrated in FIG. 5. Bulkhead 11 includes an aperture 50 into which is fitted a partially-mirrored window 51. In this embodiment, window/mirror 51 comprises a sapphire plate 5 mm thick, which is fitted such that the lower face of window/mirror 51 is approximately flush with the lower surface of bulkhead 11. The central portion of the top surface of window/mirror 51 is coated with a film of aluminum, and this portion reflects UV light incident on window/mirror 51 from below. A mirror 52 is recessed in the top surface of bulkhead 12. Mirror 52 consists of a similar plate of sapphire, 5 mm thick, its bottom surface being coated with a film of aluminum. Sapphire was chosen for window/mirror 51 and mirror 52 because it combines the properties of UV transmissibility, mechanical hardness and durability, and chemical inertness.

A broad-spectrum source 53 produces a collimated beam 54 of UV light about 5 mm in diameter. UV source 53 is advantageously the Model 4634-01 manufactured by Hamamatsu Photonics K.K. of Shizuoka-ken, Japan. It produces UV radiation in the range 190-350 nm.

A pair of mirrors 55 and 56 are positioned above aperture 50. Also mounted on the top of bulkhead 11 is a spectrometer 57, which contains a slit 58 and a diffraction grating 59. Diffraction grating 59 is advantageously the Model Chemspec 100S manufactured by American Holographic of Littleton, Mass. Positioned above spectrometer 57 is a diode array 60, which is advantageously the Model 512 DDA manufactured by EG&G Reticon of Sunnyvale, Calif. Diode array 60 uses a controller, which is advantageously the Model ST121 manufactured by Princeton Instruments, Inc. of Trenton, N.J.

When cylinder 17 is in position at Station 2, beam 54 from UV source 53 is reflected from mirror 55 through the transparent (unmirrored) portion of window 51. Mirror 55 is positioned in a precise manner such that beam 54 strikes mirror 52 and then is reflected from the central, mirrored portion of window/mirror 51. Beam 54 is then reflected repeatedly between mirror 52 and window/mirror 51 until it emerges from cylinder 17 at the far, transparent portion of window/mirror 51. Advantageously, the total length of the path of beam 54 in cylinder 17 should be on the order of 1.6 meters. Assuming that cylinder 17 is about 20 cm long, this means that beam 54 traverses the length of cylinder 17 eight times. In accordance with conventional UV absorption principles, certain wavelengths of beam 54 are absorbed by the vapors in cylinder 17, yielding a characteristic "spectrum" of the light that emerges through window/mirror 51.

UV beam 54 then strikes mirror 56 which reflects it through slit 58 to diffraction grating 59. In a conventional manner, diffraction grating 59 reflects the constituent wavelengths of beam 54 at different angles to diode array 60. Diode array 60 detects the spectrum that is characteristic of the vapors captured in cylinder 17. As described below, the spectrum detected by diode array 60 and sent to a computer by a controller is then compared with the spectrum which is obtained when cylinder 17 is free of contaminants. The differences between the two spectra are therefore attributable to UV absorption by the contaminants in cylinder 17. By this technique, different types of organic vapors are recognized and distinguished and, in particular, vapors resulting from product residues are distinguished from those which result from contaminants.

Figure 6:
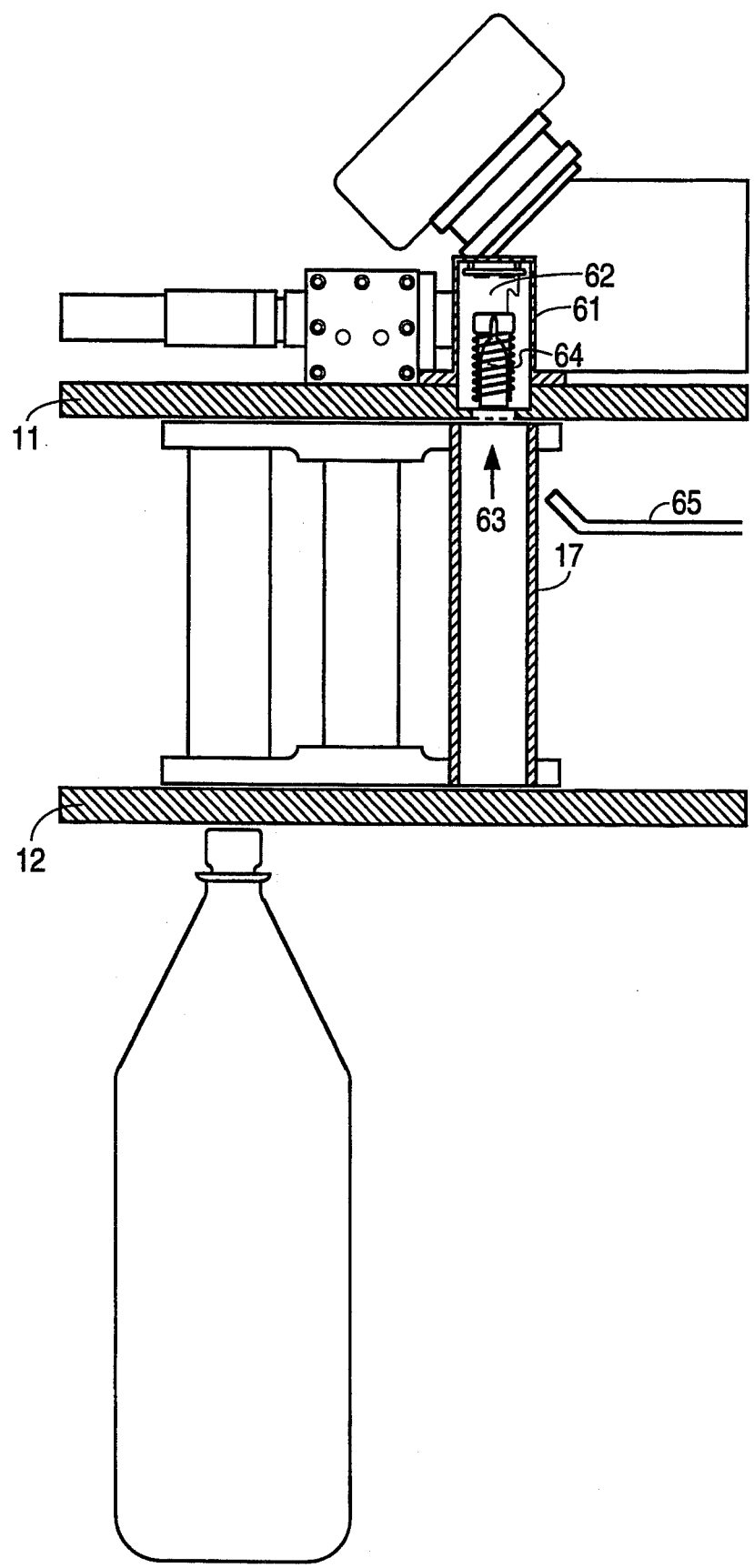
FIG. 6 illustrates a cross-sectional view of the fast photoionization detector.

Cylinder 17 is next rotated to Station 3, where it is analyzed by FPID analyzer 22. FIG. 6 illustrates a cross-sectional view of FPID analyzer 22. Included are an enclosure 61 which forms a chamber 62 and an aperture 63 formed in bulkhead 11. A UV light source 64 is positioned in chamber 62. A tube 65 is connected to a supply of pressurized air through a solenoid valve (not shown). Tube 65 is positioned so as to direct a blast of air into aperture 63 while cylinder 17 is in the process of rotation.

Figure 7:
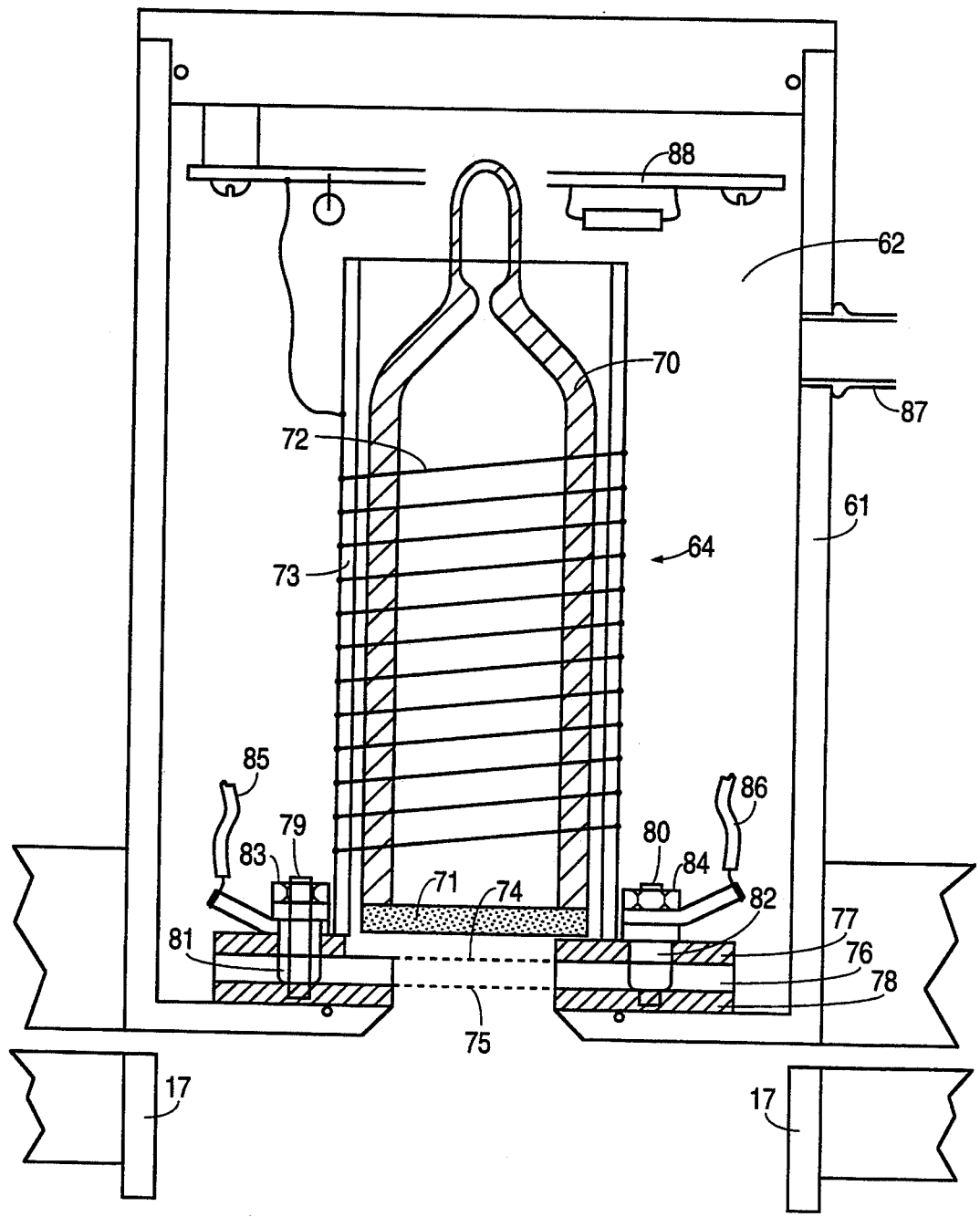
FIG. 7 illustrates a detailed cross-sectional view of the photoionization detector.

FIG. 7 illustrates a detailed cross-sectional view of FPID analyzer 22. UV source 64 is a variant of the UV source described in U.S. Pat. No. 4,413,185 to Leveson, which is incorporated herein in its entirety. Included are a discharge tube 70 which is filled with krypton and which is enclosed at one end by a magnesium fluoride window 71. An induction coil 72 is supported on a polytetrafluoraethylene cylinder 73 and powered by a radio-frequency oscillator circuit 88.

As described in U.S. Pat. No. 4,413,185, the electromagnetic field induced by coil 72 ionizes the gaseous mixture in discharge tube 70, and UV radiation is produced. The UV radiation is transmitted downward through window 71.

Beneath window 71 are positioned two electrodes 74 and 75, each of which in the preferred embodiment consists of a fine stainless steel mesh. Electrodes 74 and 75 are electrically isolated from ground and from each other by a polytetrafluorethylene spacer 76, and the assembly is held together by metallic rings 77 and 78. Metallic rings 77 and 78 are in turn clamped by metallic studs 79 and 80, which are attached mechanically and electrically to ring 78. Studs 79 and 80 are fitted with insulating bushings 81 and 82, to prevent them from shorting electrodes 74 and 75, and with nuts 83 and 84. Electrical contact is made with electrode 74 by means of a lead 85, which is in contact with metallic ring 77. Electrical contact is made with electrode 75 by means of a lead 86, which is in contact with metallic stud 80 attached to ring 78. In the preferred embodiment, electrode 75 is maintained at a positive voltage of 120 volts relative to ground and to electrode 74. Electrode 74 is connected to a sensitive amplifier system which has its input at virtual ground, the output of which represents the output of FPID analyzer 22. The amplifier is advantageously an electrometer circuit using the Model LH0042CH operational amplifier manufactured by National Semiconductor Corporation of California.

In the preferred embodiment, chamber 62 communicates with a duct 87 which is connected to a source of low pressure air, creating a slight suction in chamber 62.

When cylinder 17 arrives at Station 3, the vapors contained in the cylinder diffuse upwards into the region between electrodes 74 and 75. Owing to the minimal clearance between bulkheads 11 and 12 and disks 16 and 15, respectively, there has been minimal leakage from cylinder 17 as it passes from Station 1 to Station 3. The diffusion process is aided by the suction applied to duct 87, which draws the vapors through the electrodes, through cutouts in ring 77, and up between discharge tube 70 and cylinder 73.

As the vapor molecules enter the region between electrodes 74 and 75, some of them are ionized by the UV light from source 64. When this happens, the positive ions are attracted to electrode 74 where they are detected by the sensitive amplifier system.

Tests indicate that product residues (e.g., soft drink residues) produce a relatively small current as compared with the current produced by organic contaminants. A relatively large current is therefore interpreted as an indication that the bottle is contaminated.

Figure 9:
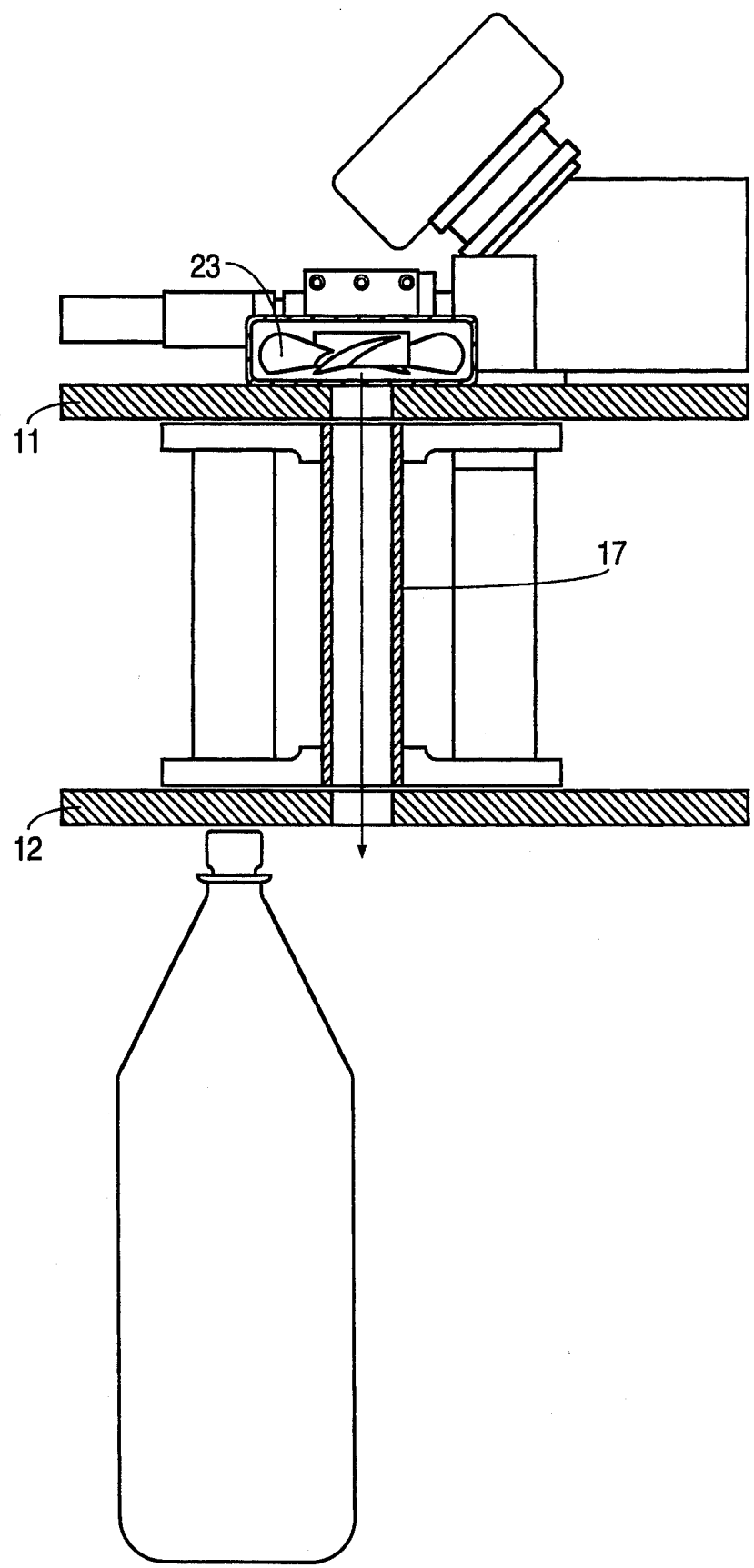
FIG. 9 illustrates a cross-sectional view of the purge station of the analyzer.

Next, the stepper motor moves cylinder 17 to Station 4, illustrated in the cross-sectional view of FIG. 9, where fan 23 expels the vapor samples from the cylinder. Alternatively, the vapors could be expelled with a blast of clean air from a nozzle. The stepper motor then rotates cylinder 17 back to Station 1, and the process is repeated. As will be evident, cylinders 17 are all used simultaneously and thus one of cylinders 17 is always positioned at each of Stations 1-4.

Figure 8:
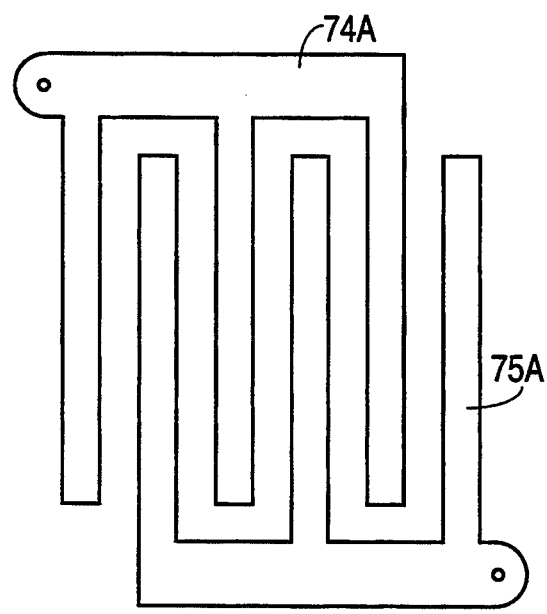
FIG. 8 illustrates a pair of interleaved electrodes that can be used in the photoionization detector.

Various configurations can be substituted for the meshes used to form electrodes 74 and 75. For example, two arrays of parallel wires could be used, or a coplanar array of interleaved elements, as shown in FIG. 8, could be used.

Figure 10:
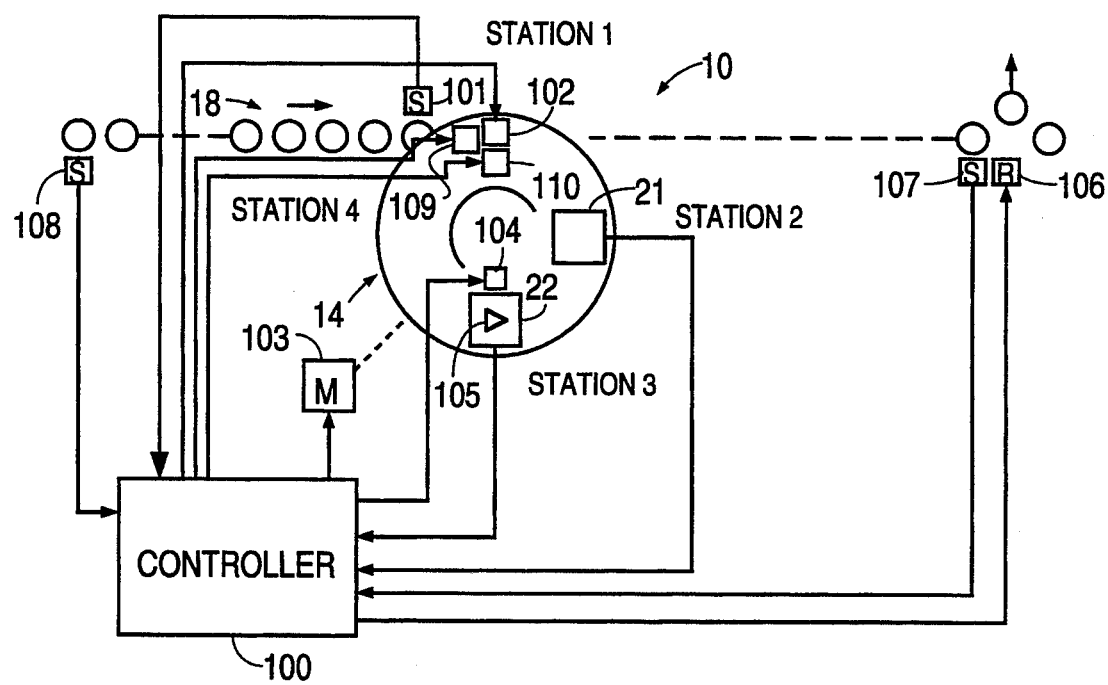
FIG. 10 illustrates a block diagram of the control network associated with the container analyzer.

FIG. 10 illustrates the control system for the bottle analyzer 10. The control function is performed by a controller 100, which is advantageously a computer. As a bottle 18 approaches the analyzer, a proximity switch 101 detects its presence and alerts controller 100. Controller 100 then triggers a solenoid valve 102 at Station 1, which delivers a burst of clean air through nozzle 41 (FIG. 4). Movement of carousel unit 14 is controlled by a stepper motor 103. After the blast of air has been delivered into the bottle, controller 100 instructs stepper motor 103 to rotate carousel 14 one-quarter turn, until the cylinder 17 reaches Station 2.

When the cylinder arrives at Station 2, controller 100 directs UVA analyzer 21 to generate a transmission spectrum of the sample within the chamber. This spectrum is then compared with a transmission spectrum recently obtained from a sample of clean air. The difference between these two spectra is then determined, and this difference spectrum represents the absorption spectrum of the sample. Measurements taken from specific parts of the sample absorption spectrum are compared by controller 100 against measurements previously taken from the absorption spectra from product residues and specific contaminants. Controller 100 applies a criterion for rejection to these measurements to determine whether an impurity is present and, if so, a "reject" decision is stored.

The transmission spectrum obtained by reading the charge on each diode in diode array 60 (FIG. 5) is compared with the transmission spectrum from clear air stored in the controller 100 to obtain an absorption spectrum for the sample. The slope of this absorption spectrum at specific regions (190 to 205 nm for gasoline) is compared with the slopes stored from previous analyses of product residues and contaminants. Tests indicate that, generally speaking, product residues have a positive slope in their absorption spectra between 190 nm and 205 nm, and that spectra of specific contaminants such as gasoline have a negative slope in this same region. A relatively negative slope is therefore interpreted as an indication that the bottle is contaminated with gasoline and is to be rejected. The specific regions are determined by experiment to be those that show the largest difference for product and contaminant. If the slope of the sample absorption spectrum is like that of the contaminant (and unlike that of the product residue), the sample is to be rejected. A "reject" decision may be based on any distinctions between the spectra of product residues and contaminants.

Controller 100 next instructs stepper motor 103 to rotate carousel 14 another one-quarter turn, bringing the cylinder 17 to Station 3. During this rotation, controller 100 causes a solenoid valve 104 to open, releasing clean air through tube 65 (FIG. 6) into the aperture 63 of FPID analyzer 22 in order to remove any residual ionizable gases from the region between electrodes 74 and 75. As noted above, FPID analyzer 22 contains a sensitive amplifier which detects a small current flow between electrodes 74 and 75 indicating the presence of an ionizable vapor. This amplifier is shown as amplifier 105 in FIG. 10. As cylinder 17 is turning from Station 2 to Station 3, controller 100 takes a reading from amplifier 105 to provide a "zero" value for FPID analyzer 22.

When cylinder 17 reaches Station 3, controller 100 samples the maximum response from FPID analyzer 22 and subtracts this from the previously stored zero value to obtain a reading for the level of ionizable material. This level is then compared with a stored value which is the maximum level to be expected if the sample contains only residual product. If this maximum value is exceeded, controller 100 determines that a contaminant is present and a "reject" decision is stored. As noted above, the decision to reject a bottle on the basis of the reading in FPID analyzer 22 is made solely on the basis of the level of the response. No attempt is made to determine which contaminant is present. It has been found that product residues generally provide low response levels, and thus if the response exceeds these threshold levels a decision is made to reject the bottle.

Figure 11:
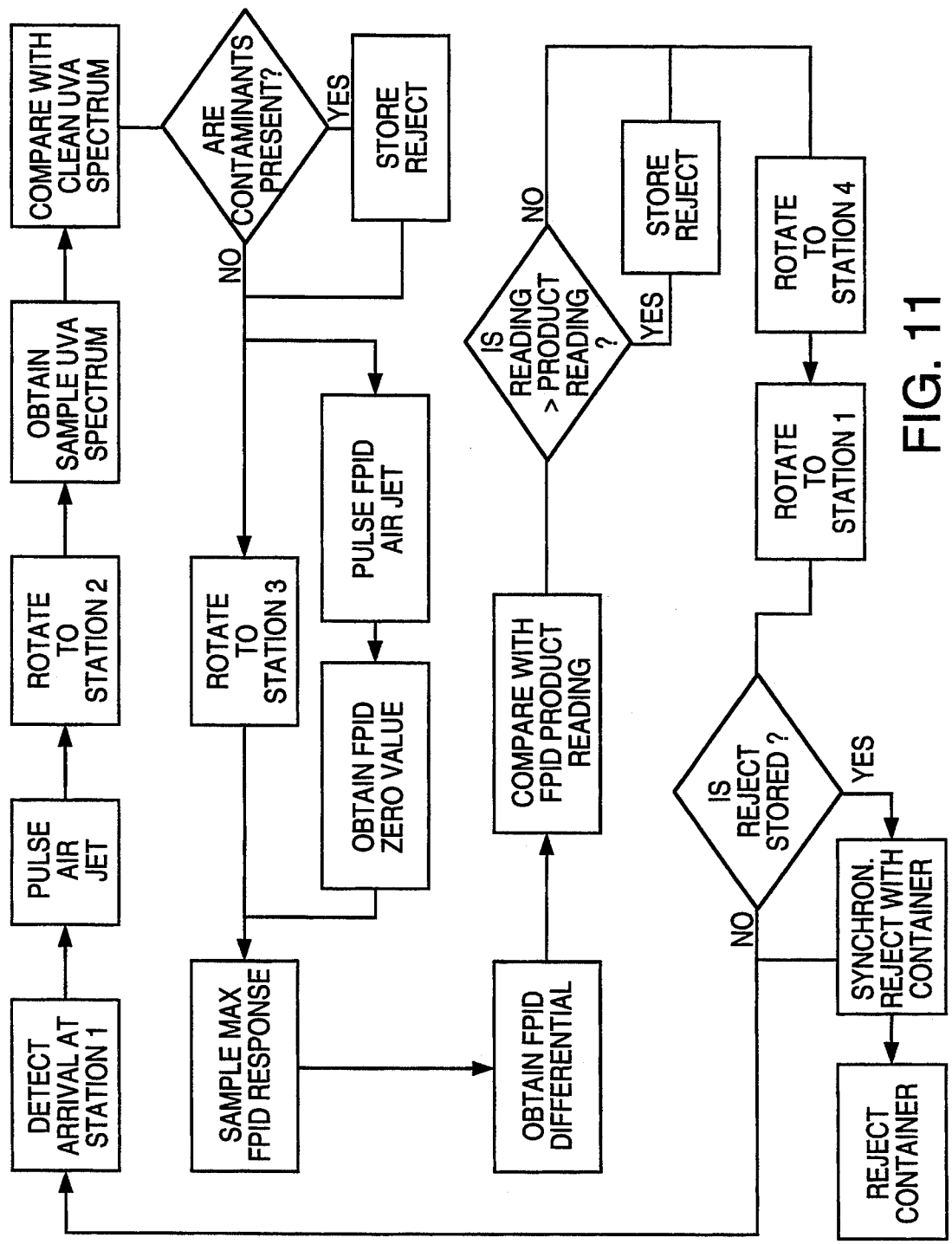
FIG. 11 illustrates a flow-chart of the program used to control the container analyzer.

If a "reject" decision is made in either UVA analyzer 21 or FPID analyzer 22, that decision is stored in controller 100 and controller 100 transmits a "reject" command to a reject mechanism 106 which is located downstream from the bottle analyzer. A proximity switch 107 alerts controller 100 to the arrival of the contaminated bottle. Each bottle sampled is assigned a sequential number by controller 100. The results (accept or reject) of the UVA and FPID analyses are stored with the corresponding bottle number when they have been determined. As each bottle passes the proximity switch 107, the controller checks the analysis results and, if the bottle is to be rejected, directs reject mechanism 106 to remove the bottle. The sequential number assigned to this bottle can then be reassigned to the next bottle to be analyzed. FIG. 11 illustrates a flow chart of the program run in controller 100.

Both UVA analyzer 21 and FPID analyzer 22 should be periodically calibrated in order to assure that the reject decisions made are correct. UVA analyzer 21 is subject to drift and to the buildup of dirt on the surfaces of windows 51 and 52 (FIG. 5). As noted previously, a spectrum must be taken by UVA analyzer 21 when cylinder 17 is free of contamination. This is necessary in order to obtain a "difference spectrum" i e an absorption spectrum due only to components in the sample not found in clean air. This contaminant-free spectrum is stored in controller 100 and is refreshed periodically by taking advantage of a gap in the bottle line. An upstream proximity switch 108 detects a gap in the bottle line and alerts controller 100. When this happens, controller 100 triggers a solenoid valve 109 at Station 1 when the "gap" arrives at the bottle analyzer 10. Solenoid valve 109 releases a volume of clean air through tube 25 (FIG. 3) into cylinder 17. When cylinder 17 is rotated to Station 2, the reading obtained from UVA analyzer 21 is stored and replaces the previously stored contaminant-free spectrum.

The reject level in FPID analyzer 22 should also be calibrated periodically. In the preferred embodiment, the gas isobutylene is used as a standard, and a "reject" decision is triggered if cylinder 17 is filled with at least 60 parts of isobutylene per million parts of air by volume (60 ppm) or the response equivalent thereof. The value of 60 ppm is based upon experience with residual products and may be varied according to further experience.

As noted previously, FPID analyzer 22 is periodically "zeroed" by directing a jet of clean air into aperture 63 prior to each analysis. When proximity switch 108 detects that two or more bottles in the line are missing, it so notifies controller 100. When this "gap" arrives at Station 1, controller 100 directs a solenoid valve 110 to open, releasing a volume of isobutylene gas into cylinder 17 through tube 25. The volume of gas released is sufficient to yield a concentration of 60 ppm in cylinder 17. When cylinder 17 arrives at Station 3, FPID analyzer 22 generates a maximum response from the sample, and the previously stored "zero" value is subtracted. The current sensed by amplifier 105 therefore represents a reading of 60 ppm isobutylene, and this determines the threshold level for rejection.

While the foregoing discussion traced the progress of a single cylinder 17 from Station 1 to Station 4, controller 100 controls all four cylinders 17 simultaneously. For example, when one cylinder is being subjected to FPID analysis at Station 3, the following cylinder is undergoing UVA analysis at Station 2.

Certain contaminants which may be present in returned bottles include ammonium compounds that are dissolved in an aqueous residue. If the ammonium radical remains chemically-bound in this manner, it has been found that UVA or FPID analysis alone will probably not be effective.

Figure 12:
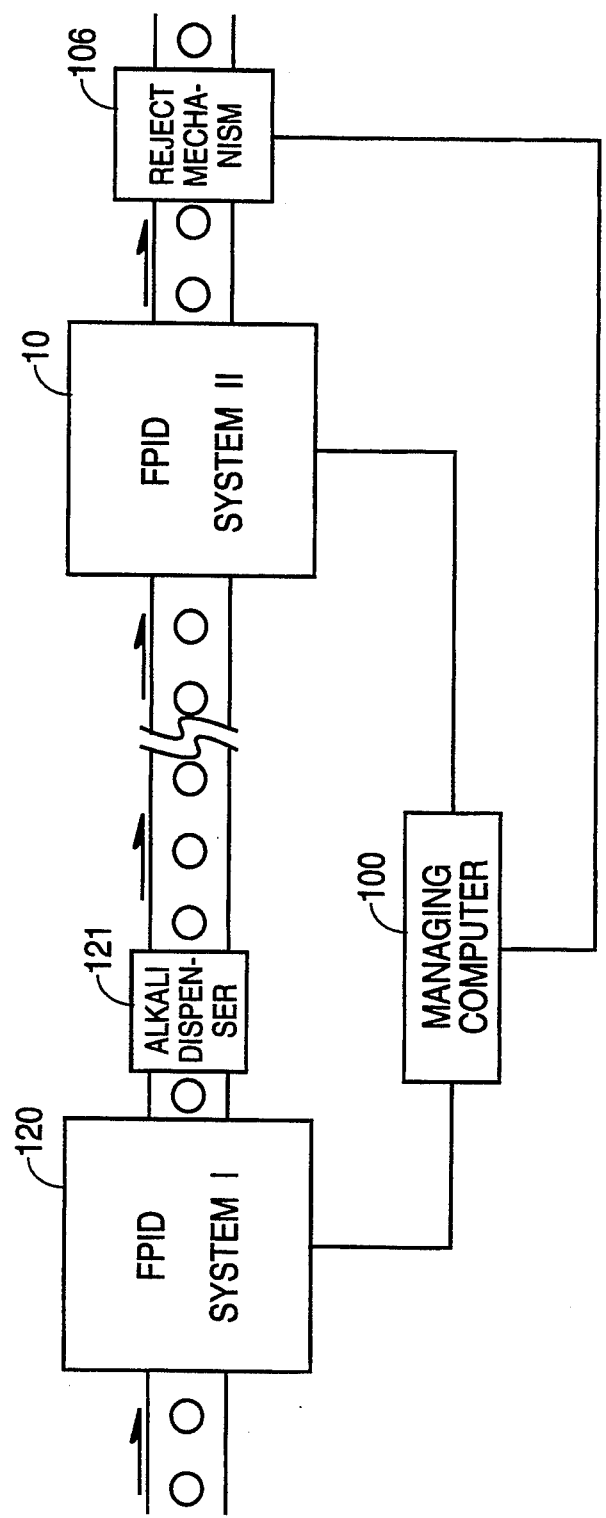
FIG. 12 illustrates a block diagram of an embodiment used to detect bound ammonium radicals.

FIG. 12 illustrates an arrangement which may be used to detect these chemically-bound ammonium radicals. Bottle analyzer 10 is identical to the bottle analyzer illustrated in FIGS. 1-9. A second bottle analyzer 120 is positioned upstream from analyzer 10 in the bottle line. Bottle analyzer 120 is similar to bottle analyzer 10 in overall structure, but UVA analyzer 21 is omitted. Bottle analyzer 120 accordingly has three sample collection cylinders and three stations, corresponding to Station 1, Station 3 and Station 4 in bottle analyzer 10.

A short distance downstream from bottle analyzer 120 is an alkali dispenser 121. Reject mechanism 106 is positioned downstream from bottle analyzer 10, and the arrangement is controlled by controller 100.

Figure 13:
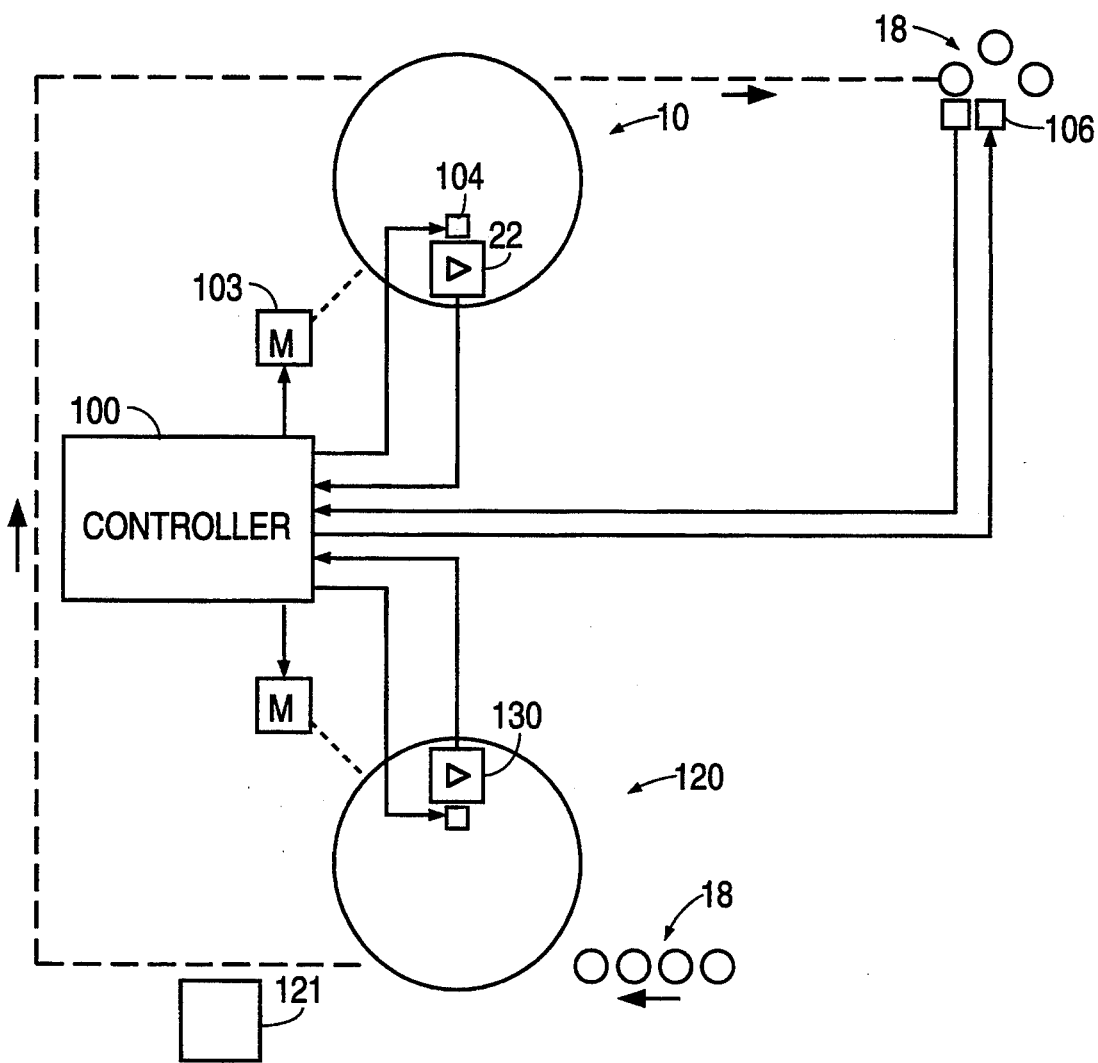
FIG. 13 illustrates a block diagram of the control network associated with the embodiment of FIG. 12.

FIG. 13 is a more detailed block diagram showing the connections between the FPID analyzers in bottle analyzers 10 and 120 and controller 100. Bottle analyzer 120 contains an FPID analyzer 130 which is similar to FPID analyzer 22. In the manner described above, FPID analyzer 130 provides an output to controller 100 representative of the level of contamination in one of cylinders 17. This information is stored in controller 100, together with the identity of the bottle whose contents were sampled. The bottle then proceeds past alkali dispenser 121 which adds a metered quantity of a strongly alkaline solution such as sodium hydroxide to the bottle. If the bottle contains chemically-bound ammonium radicals, this will release ammonia gas according to the following reaction.

$$NH_4X + NaOH \rightarrow NH_3(g) + NaX + H_2O$$

In this equation, X is one of many possible anions, organic and inorganic, associated with the ammonium radical.

It takes several seconds for the bottle to travel from alkali dispenser 121 to analyzer 10. This allows a substantial amount of ammonia gas to be produced, and the sample collected by analyzer 10 contains this gas. The ammonia gas will be ionized by FPID analyzer 22, and will produce a significantly higher output than the output registered by FPID analyzer 130 for the same bottle. Computer 100 keeps track of the identity of the bottles and compares the readings from the two FPID analyzers. From experience, it has been found that a reading from analyzer 22 that is at least 10 percent higher than the reading from analyzer 130 indicates the presence of chemically-bound ammonium radicals in the bottle residue. Controller 100 compares the two readings, and where appropriate issues a "reject" direction to reject mechanism 106.

In an alternative embodiment, bottle analyzer 120 is omitted, and a closed-loop conveyor passes each bottle through bottle analyzer 10 twice. An alkali dispenser is included in the conveyor loop, and the readings from FPID analyzer 22 from the first and second passes through bottle analyzer 10 are compared, and a decision whether to reject the bottle is made by controller 100 in exactly the same way as that described in connection with FIG. 13.

The foregoing embodiments are intended to be illustrative and not limiting. Many additional embodiments in accordance with the invention will be evident to those skilled in the art. For example, the principles of this invention are applicable to all types of containers, whether or not they are bottles, and whether or not they are made of plastic, glass or some other material. A container analyzer in accordance with this invention may have any number of stations, and the analysis may be performed using techniques other than, or in addition to, UV absorption and photoionization. For example, the test for ammonium radicals may be performed using the technique embodied in the Model 350 Converter and Model 14A Analyzer manufactured by Thermo Environmental Instruments Incorporated of Franklin, Mass., which is incorporated herein by reference. According to this method, the ammonia is first oxidized by exposure to a catalyst (for example, a heated stainless steel, platinum or gold mesh) in the presence of oxygen or ozone. Nitric oxide is formed, and this then reacts with additional ozone in a chemiluminescent reaction, the light from which may be detected using a sensitive photomultiplier tube. This technique lends itself very well to the particular sampling method described herein.

All such alternative embodiments are included within the broad scope of this invention, as defined in the following claims.

We claim:

1. An analyzer for detecting the presence of a substance on the inside of a bottle or other container, said analyzer comprising:
   a first member and a second member, said first member having a first surface and said second member having a second surface, said second surface being substantially parallel to said first surface;
   a sample chamber, said sample chamber having a first open end and a second open end and being movably positioned between said first surface and said second surface such that said first open end is adjacent said first surface and said second open end is adjacent said second surface;
   an aperture in said second member;
   means for directing a gaseous stream substantially into a container adjacent said aperture such that a vapor or gas present in said container is driven through said aperture and into said sample chamber when said sample chamber is positioned with said second open end in fluid communication with said aperture;
   means for causing relative motion between said sample chamber and said first and second members such that said sample chamber moves in a direction parallel to said first surface and said second surface; and
   a first analytical station.

2. The analyzer of claim 1 wherein said sample chamber is mounted on a carousel unit, said carousel unit being rotatably positioned between said first and second members.

3. The analyzer of claim 1 wherein said first analytical station comprises a UV absorption analyzer, said first analytical station being located such that said sample chamber is movable to a position adjacent said first analytical station.

4. The analyzer of claim 3 wherein said first analytical station comprises a source of UV radiation, a window member, a mirror member, and a spectrometer, said window member being positioned in one of said first and second members, said mirror member being positioned in the other of said first and second members, said source of UV radiation being designed to direct a beam of UV light through said window member such that said beam is reflected from said mirror member.

5. The analyzer of claim 4 further comprising means for directing said beam of UV light to said spectrometer.

6. The analyzer of claim 1 wherein said first analytical station comprises a photoionization detector and a second aperture in one of said upper and lower members, said photoionization detector comprising an analytical chamber communicating with said second aperture, a first electrode and a second electrode, said first and second electrodes being positioned adjacent said second aperture, a source of UV radiation for directing UV radiation to a region between said first and second electrodes, and a means for detecting an electrical current in one of said first and second electrodes.

7. The analyzer of claim 6 further comprising suction means for drawing a gas through said second aperture into said first analytical chamber.

8. The analyzer of claim 1 wherein said first analytical station comprises a UV absorption analyzer, said analyzer of claim 1 further comprising a second analytical station, said second analytical station comprising a photoionization detector, said sample chamber being movable to said first and second analytical stations.

9. A combination comprising:
the analyzer of claim 8;
a container line; and
a controller connected to said first and second analytical stations and to a bottle reject mechanism;
said UV absorption analyzer and said photoionization detector being for determining the quality and/or quantity of said substance in a container, said controller being for determining whether said quality and/or quantity meets or exceeds one or more predetermined criteria, and for issuing a reject instruction to said reject mechanism if said quality and/or quantity meets or exceeds one or more of said criteria.

10. An analyzer for analyzing the contents of a container, said analyzer comprising:
an upper bulkhead and a lower bulkhead, said upper bulkhead having a lower surface and said lower bulkhead having an upper surface, said upper and lower surfaces being parallel to each other;
a carousel unit rotatable between said upper and lower bulkheads, said carousel comprising a sample chamber, said sample chamber having an upper opening adjacent said upper bulkhead and a lower opening adjacent said lower bulkhead;
an aperture in said lower bulkhead;
means for propelling a gaseous stream into a container positioned adjacent said aperture so as to create a flow of gas from said container into said sample chamber;
an analytical station; and
means for rotating said carousel unit to a position in which said sample chamber is adjacent said analytical station.

11. The analyzer of claim 10 wherein said analytical station comprises an instrument selected from the group consisting of a UV absorption analyzer, a photoionization detector and an ammonium detector.

12. The analyzer further of claim 10 wherein said analyzer comprises a plurality of analytical stations.

13. The analyzer further of claim 10 wherein said analyzer comprises a plurality of sample chambers, each of said sample chambers being positioned in said carousel unit and having an upper opening adjacent said upper bulkhead and a lower opening adjacent said lower bulkhead.

14. The analyzer of claim 13 further comprising a plurality of analytical stations wherein one of said analytical stations comprises a UV absorption analyzer and another one of said analytical stations comprises a photoionization detector.

15. A system for analyzing in sequence the contents of a line of containers, said system comprising:
the analyzer of claim 1;
a container conveyor;
a container reject device; and
a controller, wherein said controller comprises a means for assigning an identification symbol to a container, a means for storing an output from said analyzer representative of the contents of a container, means for determining whether said output exceeds a predetermined threshold value, and a means for actuating said container reject device.

16. The system of claim 15 wherein said analyzer further comprises a UV absorption analyzer.

17. The system of claim 15 wherein said analyzer further comprises a photoionization detector.

18. An apparatus for analyzing the gas in a container comprising:
a support structure having a first surface and a second surface parallel to said first surface said first and second surfaces being fixed with respect to each other;
a sample chamber interposed between said first surface and said second surface, said sample chamber having a first open end adjacent said first surface and a second open end adjacent said second surface;
an aperture in said second surface;
a sampling station;
at least one analytical station; and
means for causing motion of said sample chamber between said sampling station and said at least one analytical station.

19. The apparatus of claim 18 comprising a plurality of analytical stations wherein one of said at least one analytical stations uses a technique different from another of said at least one analytical stations.

* * * * *